US012404192B2

(12) United States Patent
Ding et al.

(10) Patent No.: US 12,404,192 B2
(45) Date of Patent: Sep. 2, 2025

(54) HIGH-LOAD ORGANIC WASTEWATER DARK FERMENTATION BIOHYDROGEN PRODUCTION DEVICE AND HYDROGEN PRODUCTION METHOD

(71) Applicant: Harbin Institute of Technology, Heilongjiang (CN)

(72) Inventors: Jie Ding, Heilongjiang (CN); Nanqi Ren, Heilongjiang (CN); Shanshan Yang, Heilongjiang (CN); Defeng Xing, Heilongjiang (CN); Hanjun Sun, Heilongjiang (CN)

(73) Assignee: HARBIN INSTITUTE OF TECHNOLOGY, Heilongjiang (CN)

( * ) Notice: Subject to any disclaimer, the term of this patent is extended or adjusted under 35 U.S.C. 154(b) by 0 days.

(21) Appl. No.: 18/894,511

(22) Filed: Sep. 24, 2024

(65) Prior Publication Data
US 2025/0136485 A1    May 1, 2025

(30) Foreign Application Priority Data
Nov. 1, 2023    (CN) .......................... 202311440308.3

(51) Int. Cl.
C02F 3/28 (2023.01)
C12M 1/00 (2006.01)
C12M 1/107 (2006.01)

(52) U.S. Cl.
CPC ............. C02F 3/286 (2013.01); C12M 23/36 (2013.01); C12M 27/20 (2013.01); C12M 29/18 (2013.01);
(Continued)

(58) Field of Classification Search
CPC ............... C02F 3/286; C02F 2203/002; C02F 2303/10; C12M 23/36; C12M 27/20; C12M 29/18; C12M 47/10; C12M 21/04
(Continued)

(56) References Cited

U.S. PATENT DOCUMENTS
2018/0079672 A1* 3/2018 Meyer ................ B01D 53/1475

FOREIGN PATENT DOCUMENTS
CN    101177660 A    5/2008
CN    108651342 A    10/2018
(Continued)

OTHER PUBLICATIONS
Machine-generated English translation of CN 112939216, generated on Jun. 1, 2025.*

Primary Examiner — Fred Prince
(74) Attorney, Agent, or Firm — NKL Law; Allen Xue

(57) ABSTRACT

A high-load organic wastewater dark fermentation biohydrogen production device and a hydrogen production method are provided. An exhaust port of the production device is communicated with a gas collection region through a gas pipe; a return inlet is arranged at a bottom; a baffle plate is arranged in a two-phase separation device; the baffle plate has a helical shape that makes influent water form a helical centripetal water flow path; one end of an inert gas communicating pipe is connected with an air hole at a bottom of the gas collection region; the other end of the inert gas communicating pipe is communicated with an air intake disc; the inert gas communicating pipe is provided with a connecting hole and an air pump; and the gas collection region is connected with a gas buffer tank and a hydrogen storage tank in sequence. A two-phase separation unit is also provided.

8 Claims, 2 Drawing Sheets

(52) U.S. Cl.
CPC ....... C12M 47/10 (2013.01); *C02F 2203/002* (2013.01); *C02F 2303/10* (2013.01); *C12M 21/04* (2013.01)

(58) Field of Classification Search
USPC .......................... 210/603, 631, 252, 259, 260
See application file for complete search history.

(56) References Cited

FOREIGN PATENT DOCUMENTS

| | | | | |
|---|---|---|---|---|
| CN | 109516518 A | | 3/2019 | |
| CN | 213221295 U | | 5/2021 | |
| CN | 112939216 A | * | 6/2021 | ............ C12M 21/04 |
| WO | 2018234695 A1 | | 12/2018 | |

* cited by examiner

HIGH-LOAD ORGANIC WASTEWATER DARK FERMENTATION BIOHYDROGEN PRODUCTION DEVICE AND HYDROGEN PRODUCTION METHOD

TECHNICAL FIELD

The present invention relates to a hydrogen production reaction apparatus and a method for hydrogen production using same.

BACKGROUND

Biohydrogen production is a process of hydrogen energy production from microorganisms by using organic substrates through fermentation. In this process, the organic substrates and multiple mesostates exist in a liquid phase environment simultaneously. The viscosity of these organic components is greater than the viscosity of pure water. Because intermolecular hydrogen bonds are increased due to multiple organic components included in the liquid phase, the intermolecular force is increased. The viscosity of the liquid phase is increased obviously compared with the pure water due to the increase of the intermolecular force. Hydrogen is produced in the liquid phase and needs to be precipitated from the liquid phase for collection. According to the analysis from the mechanical principle, to precipitate hydrogen from the liquid phase, the hydrogen bubbles must overcome the gravity and the resistance of a gas-liquid phase interface during floating. As the viscosity of the liquid phase is increased, the resistance during floating of hydrogen is increased obviously. Therefore, it is more difficult to precipitate hydrogen. Because the viscosity of the microorganism that participates in the liquid phase is often much higher than the viscosity of water at the same temperature and pressure, the generated tiny hydrogen bubbles are adsorbed in the liquid phase, and are difficult to quickly and completely separate from the liquid phase. Thus, the actual amount of collected hydrogen is far less than a theoretical value, thereby limiting the further improvement of hydrogen production.

SUMMARY

The purpose of the present invention is to solve the problem that the microbial floc anaerobic active sludge existing in the traditional fermentation biohydrogen production reaction apparatus cannot quickly separate solid, liquid and gas, leading to sludge loss and low hydrogen production efficiency, to provide a high-load organic wastewater dark fermentation biohydrogen production device capable of quickly and fully conducting two-phase separation for the gas-containing high-viscosity liquid generated in the process of biohydrogen production.

The high-load organic wastewater dark fermentation biohydrogen production device in the present invention comprises a dark fermentation biohydrogen production device, a two-phase separation device, a gas buffer tank and a hydrogen storage tank; organic wastewater is used as a fermentation substrate in the dark fermentation biohydrogen production device; an exhaust port located at a top of the dark fermentation biohydrogen production device is communicated with a gas collection region through a gas pipe; and a return inlet is arranged at a bottom of the dark fermentation biohydrogen production device.

A water inlet is arranged at a side wall of the two-phase separation device; one end of a liquid inlet pipe is connected with a liquid outlet of the dark fermentation biohydrogen production device, and the other end of the liquid inlet pipe is connected with the water inlet of the two-phase separation device; a baffle plate is arranged in the two-phase separation device; the baffle plate has a helical shape that makes influent water form a helical centripetal water flow path; a return outlet is arranged at the center of a bottom plate of the two-phase separation device; the return outlet is communicated with the return inlet of the dark fermentation biohydrogen production device through a sludge return pipeline; an air intake disc is arranged below the baffle plate; a connecting pipe located at a top of the two-phase separation device is communicated with the gas collection region; one end of an inert gas communicating pipe is connected with an air hole at a bottom of the gas collection region; the other end of the inert gas communicating pipe is communicated with the air intake disc; and the inert gas communicating pipe is provided with a connecting hole and an air pump.

A hydrogen outlet at a top of the gas collection region is connected with an air inlet of the gas buffer tank through a first air delivery pipe, and an air outlet of the gas buffer tank is connected with an inlet of the hydrogen storage tank through a second air delivery pipe.

A hydrogen production method using the high-load organic wastewater dark fermentation biohydrogen production device in the present invention is achieved according to the following steps:

I. introducing organic wastewater into the dark fermentation biohydrogen production device for anaerobic fermentation treatment; making the generated hydrogen reach the gas collection region through the gas pipe; making gas-containing high-viscosity fermentation liquid reach the two-phase separation device through the liquid inlet pipe and flow helically centripetally along the baffle plate; at the same time, introducing inert gas (argon) from the connecting hole of the inert gas communicating pipe; spraying inert gas bubbles from the air intake disc by the inert gas; applying disturbance to the gas-containing high-viscosity fermentation liquid; and making the precipitated hydrogen flow into a gas phase collection region along the connecting pipe through a mist catcher and accumulate in an upper space of the gas phase collection region;

II. flowing, by the gas-containing high-viscosity fermentation liquid, into the return outlet along the baffle plate, and returning into the dark fermentation biohydrogen production device through the sludge return pipeline;

III. flowing, by the hydrogen accumulated at the upper part of the gas phase collection region into a gas buffer tank through the first air delivery pipe, manufacturing the hydrogen in the gas buffer tank into liquid hydrogen by a compressor, and storing the liquid hydrogen into the hydrogen storage tank.

In the present invention, the fermentation biohydrogen production reactor and the two-phase separation unit are separately arranged, so that the two-phase separation unit can better play the role of gas-liquid separation, thereby improving the settling performance of active sludge. Thus, the sludge can be returned into the fermentation biohydrogen production reactor in time, thereby overcoming the problem of sludge loss of the fermentation biohydrogen production reaction apparatus. The return of the sludge increases the biomass in the system. Thus, the device has a stronger acid-base buffer capacity, so that the acidic environment of the system is greatly improved in a short time.

The high-load organic wastewater dark fermentation biohydrogen production device of the present invention generates a large number of bubbles through the air intake disc in the two-phase separation unit, which can fully precipitate hydrogen, and also generates bubbles in an inert gas exhaust hole, so that a small number of tiny hydrogen bubbles remaining in the liquid phase collection region are taken out, and the hydrogen production can be better guaranteed, thereby achieving the efficient and reasonably utilization of the biohydrogen production reaction substrate.

To sum up, the high-load organic wastewater dark fermentation biohydrogen production device in the present invention has the following beneficial effects:

1. In the present invention, the fermentation biohydrogen production reactor and the two-phase separation unit are separately arranged, so that the two-phase separation unit can better play a role, thereby improving the settling performance of active sludge. Thus, the sludge can be returned into the fermentation biohydrogen production reactor in time, thereby solving the problem of sludge loss of the fermentation biohydrogen production reaction apparatus. The return of the sludge increases the biomass in the system. Thus, the device has a stronger acid-base buffer capacity, so that the acidic environment of the system is greatly improved in a short time.
2. The sludge return pipeline of the present invention ensures high biological holding in the fermentation biohydrogen production reactor and improves the volume utilization rate of the present invention. The hydrogen production efficiency of the system is significantly better than that of the traditional hydrogen production system due to the high biological holding, high overall level of metabolism of the system for the substrate and good hydrogen production metabolic capacity of sludge fermentation.
3. At the same time, a large number of bubbles generated by the sludge flocs can be released in time, and bubbles are generated from an inert gas exhaust hole of the two-phase separation unit, and make macroscopic motion towards a free liquid surface. Thus, tiny hydrogen bubbles remaining in the liquid phase collection region are taken out. The residence time of the sludge flocs is increased through the spiral baffle plate to promote the hydrogen to quickly and fully discharge upward from the liquid phase.
4. The high-load organic wastewater dark fermentation biohydrogen production device also of the present invention also has the advantages of simple structure, stable operation, flexible operation, high volume utilization rate, high biological holding, high hydrogen production efficiency and low operating cost.

DETAILED DESCRIPTION

Figure 1:
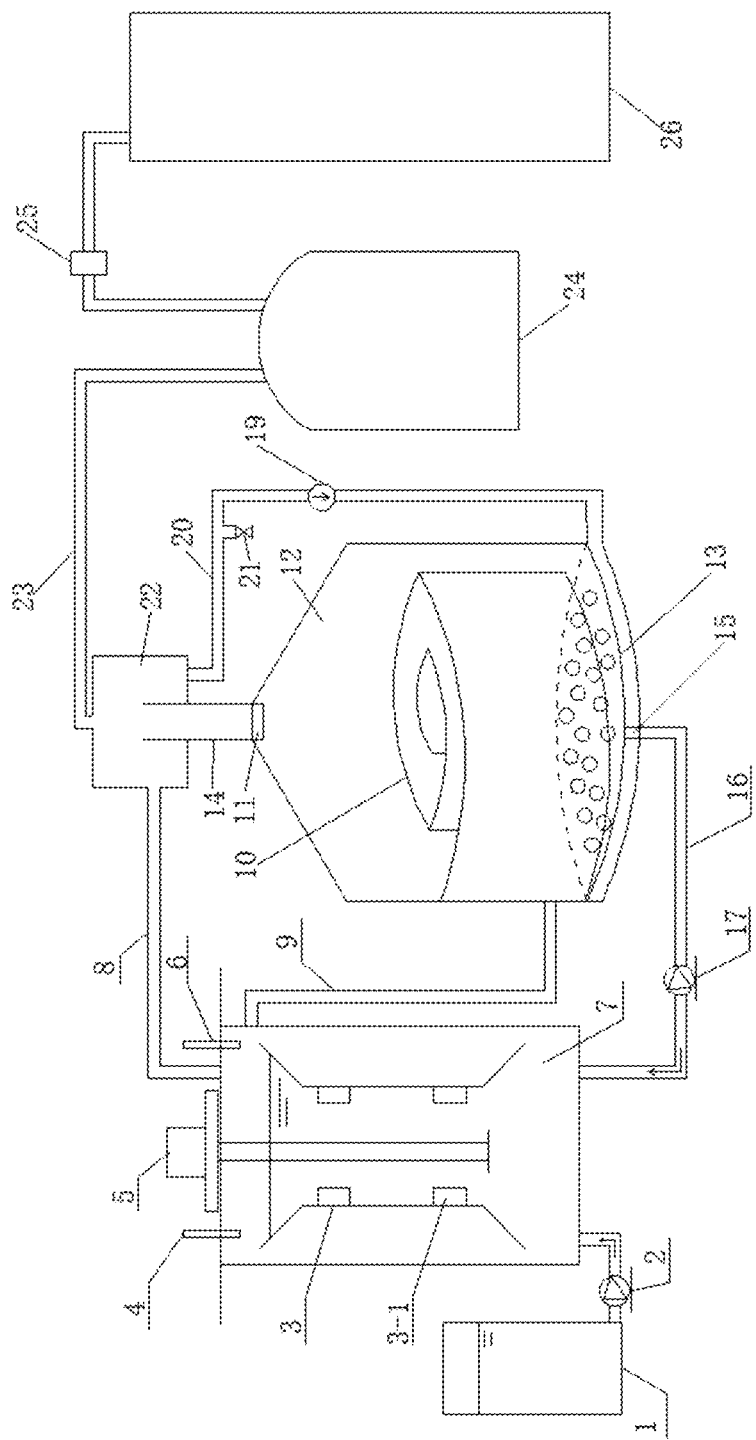
FIG. 1 is a structural schematic diagram of a high-load organic wastewater dark fermentation biohydrogen production device in the present invention.
Figure 2:
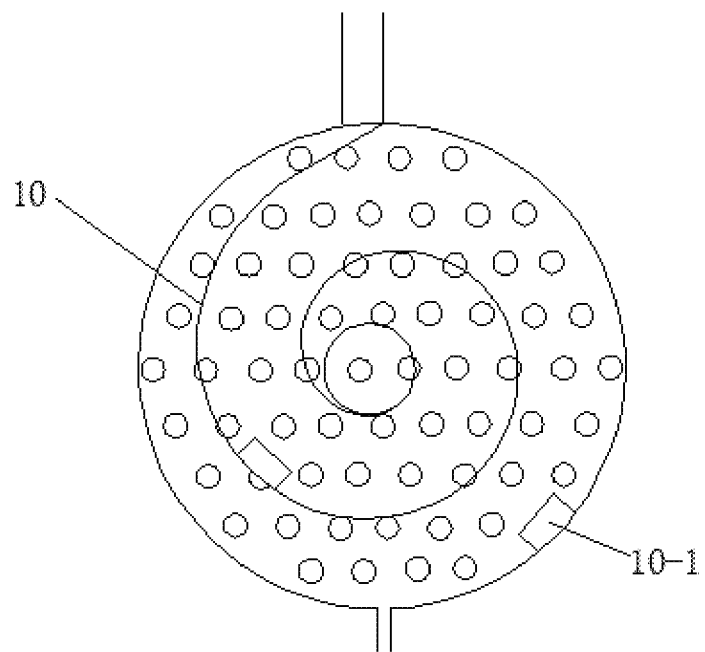
FIG. 2 is a top structural schematic diagram of a baffle plate.

Specific embodiment 1: A high-load organic wastewater dark fermentation biohydrogen production device in the present embodiment comprises a dark fermentation biohydrogen production device 7, a two-phase separation device 12, a gas buffer tank 24 and a hydrogen storage tank 26; organic wastewater is used as a fermentation substrate in the dark fermentation biohydrogen production device 7; an exhaust port located at a top of the dark fermentation biohydrogen production device 7 is communicated with a gas collection region 22 through a gas collection pipe 8; and a return inlet is arranged at a bottom of the dark fermentation biohydrogen production device 7.

A water inlet is arranged at a side wall of the two-phase separation device 12; one end of a inlet pipe 9 is connected with a liquid outlet of the dark fermentation biohydrogen production device 7, and the other end of the inlet pipe 9 is connected with the water inlet of the two-phase separation device 12; a baffle plate 10 is arranged in the two-phase separation device 12; the baffle plate 10 has a helical shape that makes influent water form a helical centripetal water flow path; a return outlet 15 is arranged at the center of a bottom plate of the two-phase separation device 12; the return outlet 15 is communicated with the return inlet of the dark fermentation biohydrogen production device 7 through a sludge return pipeline 16; an air intake disc 13 is arranged below the baffle plate 10; a connecting pipe 14 located at a top of the two-phase separation device 12 is communicated with the gas collection region 22; one end of an inert gas pipe 20 is connected with an air hole at a bottom of the gas collection region 22; the other end of the inert gas pipe 20 is communicated with the air intake disc 13; and the inert gas pipe 20 is provided with a connecting inlet 21 and an air pump 19.

A hydrogen outlet at a top of the gas collection region 22 is connected with the air inlet of the gas buffer tank 24 through a first air delivery pipe 23, and an air outlet of the gas buffer tank 24 is connected with an inlet of the hydrogen storage tank 26 through a second air delivery pipe.

Specific embodiment 2: The present embodiment differs from the specific embodiment 1 in that a thermometer 4 and an ORP probe 6 are arranged in the dark fermentation biohydrogen production device 7.

Specific embodiment 3: The present embodiment differs from the specific embodiment 1 or 2 in that a agitator 5 is arranged in the dark fermentation biohydrogen production device 7.

Specific embodiment 4: The present embodiment differs from one of the specific embodiments 1 to 3 in that organic wastewater is loaded in the water tank 1, and the water tank 1 is communicated with a liquid inlet of the dark fermentation biohydrogen production device 7 through a water inlet pipe.

Specific embodiment 5: The present embodiment differs from one of the specific embodiments 1 to 4 in that the baffle plate 10 is provided with a plurality of ultrasonic generators 10-1.

In the present embodiment, a plurality of ultrasonic generators are arranged on a plate surface of the baffle plate, and degassing is accelerated by using ultrasonic vibration of the ultrasonic generators.

Specific embodiment 6: The present embodiment differs from one of the specific embodiments 1 to 5 in that the height of the connecting pipe 14 extending into the gas collection region 22 is greater than ½ of the height of the gas collection region 22.

Specific embodiment 7: The present embodiment differs from one of the specific embodiments 1 to 6 in that a mist catcher 11 is arranged at a bottom of the connecting pipe 14.

In the present embodiment, when aerial fog flows through the mist catcher, the cross section is reduced and the gas velocity is increased; and when the aerial fog flows through a straight flow channel, the gas velocity is reduced, and the liquid accumulated to the surface is accumulated into larger droplets which flow out of a demister by gravity.

Specific embodiment 8: The present embodiment differs from one of the specific embodiments 1 to 7 in that the second air delivery pipe is provided with a compressor 25.

Specific embodiment 9: The present embodiment differs from one of the specific embodiments 1 to 8 in that the sludge return pipeline 16 is provided with a sludge metering pump 17.

Specific embodiment 10: A hydrogen production method using the high-load organic wastewater dark fermentation biohydrogen production device in the present embodiment is achieved according to the following steps:

I. introducing organic wastewater into the dark fermentation biohydrogen production device 7 for anaerobic fermentation treatment; making the generated hydrogen reach the gas collection region 22 through the gas collection pipe 8; making gas-containing high-viscosity fermentation liquid reach the two-phase separation device 12 through the inlet pipe 9 and flow helically centripetally along the baffle plate 10; at the same time, introducing inert gas (argon) from the connecting inlet 21 of the inert gas pipe 20; spraying inert gas bubbles from the air intake disc 13 by the inert gas; applying disturbance to the gas-containing high-viscosity fermentation liquid; and making the precipitated hydrogen flow into the gas collection region 22 along the connecting pipe 14 through the mist catcher 11 and accumulate in an upper space of the gas collection region 22;

II. flowing, by the gas-containing high-viscosity fermentation liquid, into the return outlet 15 along the baffle plate 10, and returning into the dark fermentation biohydrogen production device 7 through the sludge return pipeline 16;

III. flowing, by the hydrogen accumulated at an upper part of the gas collection region 22, into the gas buffer tank 24 through the first air delivery pipe 23, manufacturing the hydrogen in the gas buffer tank 24 into liquid hydrogen by the compressor 25, and storing the liquid hydrogen into the hydrogen storage tank 26.

Embodiment: A hydrogen production method using the high-load organic wastewater dark fermentation biohydrogen production device in the present embodiment is achieved according to the following steps:

I. introducing organic wastewater into the dark fermentation biohydrogen production device 7 for anaerobic fermentation treatment; making the generated hydrogen reach the gas collection region 22 through the gas collection pipe 8; making gas-containing high-viscosity fermentation liquid reach the two-phase separation device 12 through the inlet pipe 9 and flow helically centripetally along the baffle plate 10; at the same time, introducing inert gas (argon) from the connecting inlet 21 of the inert gas pipe 20; spraying inert gas bubbles from the air intake disc 13 by the inert gas; applying disturbance to the gas-containing high-viscosity fermentation liquid; and making the precipitated hydrogen flow into the gas collection region 22 along the connecting pipe 14 through the mist catcher 11 and accumulate in an upper space of the gas collection region 22;

II. flowing, by the gas-containing high-viscosity fermentation liquid, into the return outlet 15 along the baffle plate 10, and returning into the dark fermentation biohydrogen production device 7 through the sludge return pipeline 16;

III. flowing, by the hydrogen accumulated at an upper part of the gas collection region 22, into the gas buffer tank 24 through the first air delivery pipe 23, manufacturing the hydrogen in the gas buffer tank 24 into liquid hydrogen by the compressor 25, and storing the liquid hydrogen into the hydrogen storage tank 26.

The present embodiment uses the dark fermentation biohydrogen production reaction device in the specific embodiment 1, wherein a draft tube 3 with upper and lower ends of "flared shape" is arranged in the dark fermentation biohydrogen production device 7, and a agitator 5 is arranged in the draft tube 3, so that the fermentation mixed liquid can circularly flow inside and outside the draft tube. The vertical baffle plates 3-1 are uniformly, crosswise and fixedly installed on the inner wall of the flared draft tube to avoid swirling of the mixed liquid due to stirring.

In the present embodiment, the cultured active sludge is inoculated into the dark fermentation biohydrogen production device at a concentration of 20 gMLSS/L, and the artificially prepared molasses wastewater (the molasses wastewater is the organic wastewater formed by adding the waste molasses from a beet-sugar factory to the tap water, and necessary N, P and trace elements are supplemented in the test) is pumped into the dark fermentation biohydrogen production device 7 by a metering pump.

Figure 3:
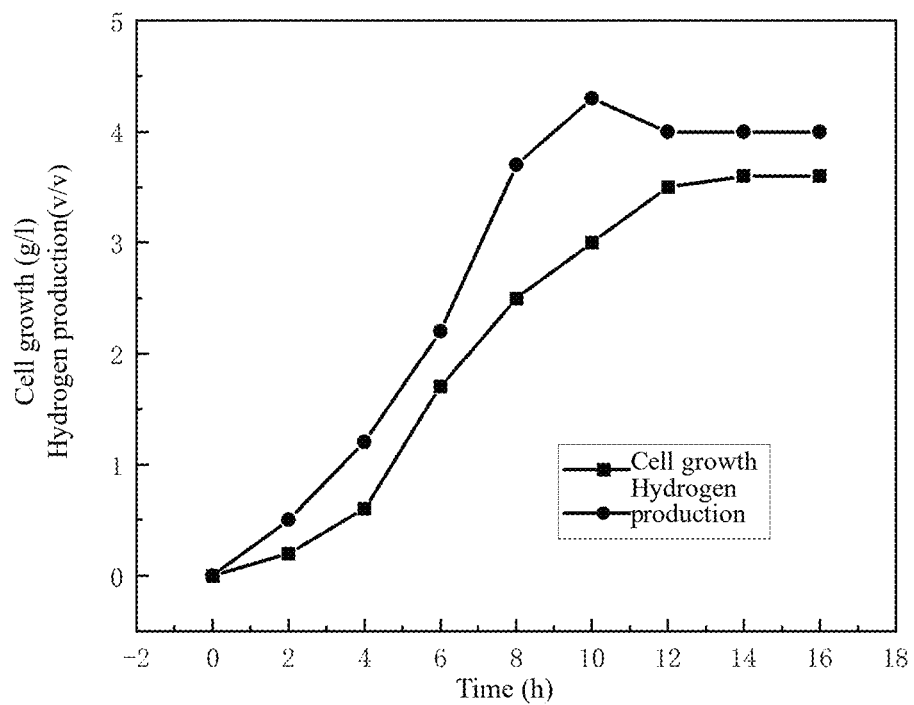
FIG. 3 is an effect diagram of hydrogen production by using a high-load organic wastewater dark fermentation biohydrogen production device in embodiment 1.

In the present embodiment, in the control engineering, the control parameter temperature is controlled as 35±1° C., and the anaerobic fermentation processing time of the dark fermentation biohydrogen production device 7 is controlled as 16 h. FIG. 3 shows the growth rate of cells and the hydrogen production, and shows that the hydrogen production reaches up to 4.3V/V at 10 h. As a result, the hydrogen content in biogas is higher than 60%. If the two-phase separation device is not arranged and only the dark fermentation biohydrogen production device is used to produce hydrogen, then the hydrogen production is only 3.62V/V, and the hydrogen production and hydrogen purity are lower than those of the present embodiment.

The dark fermentation biohydrogen production reaction device of the present invention accelerates the contact degree between microorganisms and biomass raw material, and improves the space utilization rate, thereby not only increasing the hydrogen production rate, but also improving the utilization rate of the biomass raw material. It can be considered that a new strengthening way is successfully provided for improving the efficiency of microbial hydrogen production.

What is claimed is:

1. A organic wastewater dark fermentation biohydrogen production device, comprising:
    a dark fermentation biohydrogen production device (7), a two-phase separation device (12), a gas buffer tank (24) and a hydrogen storage tank (26), wherein;
    an organic wastewater is used as a fermentation substrate in the dark fermentation biohydrogen production device (7);
    an exhaust port located at a top of the dark fermentation biohydrogen production device (7) is in fluid communication with a gas collection region (22) through a gas collection pipe (8); and
    a return inlet is arranged at a bottom of the dark fermentation biohydrogen production device (7);

a water inlet is arranged at a side wall of the two-phase separation device (12);

a first end of a inlet pipe (9) is connected with a liquid outlet of the dark fermentation biohydrogen production device (7), and a second end of the inlet pipe (9) is connected with the water inlet of the two-phase separation device (12);

a baffle plate (10) is arranged in the two-phase separation device (12), wherein the baffle plate (10) is provided with a plurality of ultrasonic generators (10-1), and the baffle plate (10) has a helical shape that makes influent water form a helical centripetal water flow path;

a return outlet (15) is arranged at the center of a bottom plate of the two-phase separation device (12);

the return outlet (15) is fluid communication with the return inlet of the dark fermentation biohydrogen production device (7) through a sludge return pipeline (16);

an air intake disc (13) is arranged below the baffle plate (10);

a connecting pipe (14) located at a top of the two-phase separation device (12) is in fluid communication with the gas collection region (22);

a first end of an inert gas pipe (20) is connected with an air hole at a bottom of the gas collection region (22), wherein a mist catcher (11) is arranged at a bottom of the connecting pipe (14), and a second end of the inert gas pipe (20) is in fluid communication with the air intake disc (13); and the inert gas pipe (20) is provided with a connecting inlet (21) and an air pump (19); and a hydrogen outlet at a top of the gas collection region (22) is connected with the air inlet of the gas buffer tank (24) through a first air delivery pipe (23), and an air outlet of the gas buffer tank (24) is connected with an inlet of the hydrogen storage tank (26) through a second air delivery pipe.

2. The organic wastewater dark fermentation biohydrogen production device according to claim 1, wherein a thermometer (4) and an ORP probe (6) are arranged in the dark fermentation biohydrogen production device (7).

3. The organic wastewater dark fermentation biohydrogen production device according to claim 1, wherein an agitator (5) is arranged in the dark fermentation biohydrogen production device (7).

4. The organic wastewater dark fermentation biohydrogen production device according to claim 1, wherein organic wastewater is loaded in a water tank (1), and the water tank (1) is in fluid communication with a liquid inlet of the dark fermentation biohydrogen production device (7) through a water inlet pipe, wherein a length of the connecting pipe (14) extending into the gas collection region (22) is greater than ½ of a height of the gas phase collection region (22).

5. The organic wastewater dark fermentation biohydrogen production device according to claim 1, wherein a length of the connecting pipe (14) extending into the gas collection region (22) is greater than ½ of a height of the gas phase collection region (22).

6. The organic wastewater dark fermentation biohydrogen production device according to claim 1, wherein the second air delivery pipe is provided with a compressor (25).

7. The organic wastewater dark fermentation biohydrogen production device according to claim 1, wherein the sludge return pipeline (16) is provided with a sludge metering pump (17).

8. A hydrogen production method using the organic wastewater dark fermentation biohydrogen production device according to claim 1, comprising the following steps:

introducing an organic wastewater into the dark fermentation biohydrogen production device (7) for anaerobic fermentation treatment; generating a gaseous hydrogen from a fermentation liquid and introducing the gaseous hydrogen to the gas collection region (22) through the gas collection pipe (8); introducing the fermentation liquid to the two-phase separation device (12) through the inlet pipe (9) along the baffle plate (10); at the same time, introducing an inert gas from the connecting inlet (21) of the inert gas pipe (20); spraying the inert gas bubbles from the air intake disc (13) by the inert gas to cause disturbance to the fermentation liquid wherein the gaseous hydrogen emitted from the fermentation liquid flow into the gas collection region (22) along the connecting pipe (14) through the mist catcher (11) and accumulate in an upper space of the gas collection region (22);

sending the fermentation liquid into the return outlet (15) along the baffle plate (10), and returning into the dark fermentation biohydrogen production device (7) through the sludge return pipeline (16); and introducing the hydrogen accumulated at an upper part of the gas collection region (22) into the gas buffer tank (24) through the first air delivery pipe (23), compressing the hydrogen in the gas buffer tank (24) into liquid hydrogen by the compressor (25), and storing the liquid hydrogen into the hydrogen storage tank (26).

\* \* \* \* \*